United States Patent [19]

Ganesan et al.

[11] Patent Number: 5,160,734
[45] Date of Patent: Nov. 3, 1992

[54] SUSTAINED RELEASE DELIVERY SYSTEM FOR SUBSTITUTED DIHYDROPYRIDINE CALCIUM CHANNEL BLOCKERS

[75] Inventors: Madurai G. Ganesan, Suffern, N.Y.; Narendra R. Desai, Danbury Fairfield, Conn.; Gary A. Maier, Orange, N.Y.; Prakash S. Kulkarni, Morris, N.J.

[73] Assignee: American Cyanamid Company, Stamford, Conn.

[21] Appl. No.: 641,610

[22] Filed: Jan. 15, 1991

Related U.S. Application Data

[63] Continuation of Ser. No. 125,440, Nov. 25, 1987, abandoned.

[51] Int. Cl.⁵ .............................................. A61K 9/22
[52] U.S. Cl. ............................... 424/78.38; 424/78.08; 514/356; 514/941; 525/403; 525/941
[58] Field of Search .................. 424/78; 514/941, 356; 525/403, 941

[56] References Cited

U.S. PATENT DOCUMENTS 3,867,521  2/1975  Miskel et al. .......................... 474/78
4,537,898  8/1985  Hoff et al. ............................. 514/941

OTHER PUBLICATIONS

Dietlin, G. A. vol. 9 #4 p. 2 (28357h).

*Primary Examiner*—Lester L. Lee
*Attorney, Agent, or Firm*—H. G. Jackson

[57] ABSTRACT

Complex of 1,4-dihydropyridine with polyoxyethylene-polyoxypropylene copolymer useful in sustained release dosage formulations.

24 Claims, 7 Drawing Sheets

SUSTAINED RELEASE DELIVERY SYSTEM FOR SUBSTITUTED DIHYDROPYRIDINE CALCIUM CHANNEL BLOCKERS

This is a continuation of application Ser. No. 07/125,440, filed Nov. 25, 1987, and now abandoned.

FIELD OF THE INVENTION

This invention is concerned with a formulation that provides for the sustained release of 1,4-dihydropyridines after oral adminsitration.

BACKGROUND OF THE INVENTION

Sustained or controlled release formulations that provide for continued release of orally administered pharmaceuticals. In the prior art these formulations have been based on coatings that are gradually eroded or dissolved. In addition, it is known to use discrete polymeric units that have been impregnated with a drug that will be slowly leached from the polymeric unit by the action of gastro intestinal fluids. In order to prepare sustained or controlled release formulations of 1,4-dihydropyridine, it is important that the drug is adequately soluble in water or in a pharmaceutically acceptable solvent in order to achieve therapeutic blood levels. It is also important that the solubility characteristics be substantially unaffected by environmental conditions (heat, light, moisture) or by the manufacturing process that is employed to make the sustained or controlled release composition. PCT application WO 83/2230 (CA 102(8) 154832) discloses dry capsules that were prepared with nifedipine, sucrose stearate, Pluronic F 68, lactose and methyl cellulose. CA 99(4): 27904d discloses a solidified melt of griseofulvin-Pluronic F 68 that shows increased bioavailability as compared to micronized griseofulvin.

The applicants have discovered that the solubility of the poorly soluble 1,4-dihydropyridines such as nilvadipine and nifedipine may be modified by forming a complex of said 1,4-dihydropyridines with a polyoxypropylene-polyoxyethylene block copolymer. These complexes have sufficient water solubility for use in the preparation of a sustained or controlled release pharmaceutical composition.

These complexes are stable over a wide temperture range and exhibit higher bioabsorbtion than presently available systems.

SUMMARY OF THE INVENTION

There are provided complexes which comprise of a 1,4-dihydropyridine with one or more polyoxypropylene-polyoxyethylene block copolymers.

Also provided by the invention are sustained release compositions of 1,4-dihydropyridine and one or more polyoxypropylene-polyoxyethylene block copolymers in combination with a material that forms a low viscosity transient gel such as a water soluble cellulose derivative.

The invention also provides a novel quick release and sustained release formulations of 1,4-dihydropyridines-complexes. By selection and blending of the water soluble cellulose derivative, it is possible to prepare dosage formulation that deliver the drugs in a bioavailable form over periods of from 10 minutes to 24 hours.

DETAILED DESCRIPTION OF THE INVENTION

Figure 1:
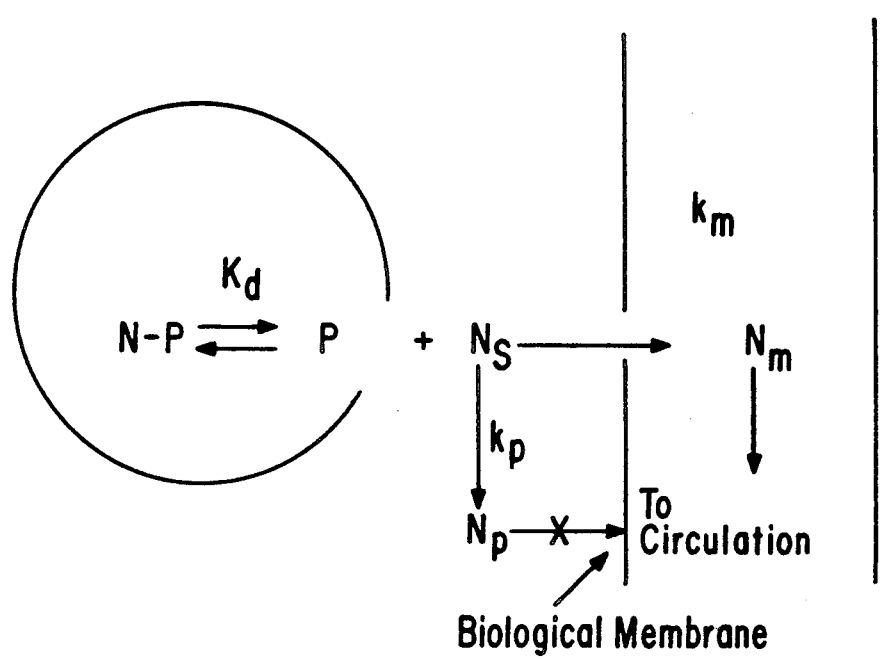
FIG. 1 is a diagram that depicts the behavior of nilvadipine-polyoxyethylene-polyoxypropylene complex.

Suitable 1,4-dihydropyridines that may be utilized in the practice of the invention include nilvidapine or its (−) or (+) enantiomers, nitredipine, nisoldipine, niludipine, nicardipine, nifedipine, and nimodipine. These types of compounds are described in U.S. Pat. Nos. 4,264,611; 4,510,150; 4,338,322; 4,284,634; 4,504,476; and 4,520,112.

Preferred 1,4-dihydropyridines include those of the general formula:

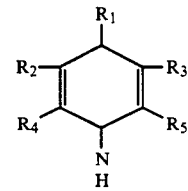

or a resolved enantiomer thereof, wherein $R_1$ is aryl which may have one or more suitable substituents(s) or a heterocyclic group, $R_2$ and $R_3$ are each, same or different, esterified carboxy, and $R_4$ and $R_5$ are each hydrogen, cyano, lower alkyl, or substituted lower alkyl in which the substituent is cyano, hydroxy, acyloxy, hydroxyimino, hydrazono, lower alkoxyimino, hydroxy(lower)alkylimino, N'- or N',N'-di(lower)alkylamino(lower)alkylimino, hydrazino, hydroxy(lower)alkylamino, N'- or N',N'-di(lower)alkylamino(lower)alkylamino, a 5 or 6-membered saturated N-containing heterocyclic-1-yl which may have hydroxy, lower alkyl or hydroxy(lower)alkyl, or oxo wherein the thus formed carbonyl may be protected with suitable protecting group; provided that, when one of $R_4$ and $R_5$ is hydrogen or lower alkyl, the other is always cyano or said substituted lower alkyl, and when $R_4$ and $R_5$ are not hydrogen or lower alkyl, both of them are a group selected from cyano and said substituted lower alkyl, or $R_4$ is hydrogen or lower alkyl and $R_3$ and $R_5$ are combined to form a group of the formula:

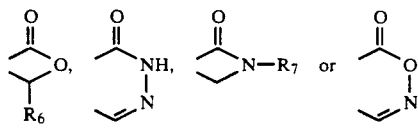

wherein $R_6$ is hydrogen or methyl and $R_7$ is 2-(N,N-diethylamino)ethyl or 2-hydroxyethyl.

The terms used in the definitions of the symbols of the general formulae given in this specification and claims are explained as follows:

The term "lower" used in connection with an alkylene, alkyl and alkenyl is intended to mean the one having 1 or 2 to 8 carbon atoms.

The aryl and aryl moieties may be phenyl, naphthyl, xylyl, tolyl, mesityl, cumenyl and the like, which may have one or more suitable substituent(s). Preferred examples of the suitable substituent(s) are halogen, nitro, hydroxy, halo(lower)-alkyl, lower alkoxy, lower alkenyloxy, cyano, lower alkoxycarbonyl or lower alkylsulfamoyl. The halogen or halo moieties are fluorine, chlorine, bromine or iodine.

Lower alkylene moieties may have a straight or branched and saturated bivalent hydrocarbon chain such as methylene, ethylene, methylmethylene, trimethylene, propylene or tetramethylene.

Lower alkyl and lower alkyl moieties may have a straight or branched and saturated hydrocarbon chain such as methyl, ethyl, propyl, isopropyl, butyl, isobutyl, t-butyl, pentyl, neo-pentyl, hexyl, heptyl or octyl.

Lower alkoxy and lower alkoxy moieties may be methoxy, ethoxy, propoxy, isopropoxy, butoxy, t-butoxy and pentyloxy.

Halo(lower)alkyl moieties may be mono-halo(lower)alkyl such as chloromethyl, bromomethyl or chloropropyl; dihalo(lower alkyl such as 1,2-dichloroethyl, 1,2-dibromoethyl or 2,2-dichloroethyl; and tri-halo(lower)alkyl such as trifluoromethyl or 1,2,2,-trichloroethyl.

Lower alkenyl and lower alkenyl moieties may be ones having a straight or branched hydrocarbon chain which contains one or more double bond(s), such as vinyl, allyl, butenyl, butanedienyl or penta-2,4-dienyl.

Acyl and acyl moieties may be lower alkanoyl such as formyl, acetyl, propionyl, butyryl, isobutyryl, valeryl, isovaleryl, pivaloyl; substituted lower alkanoyl, for example, carboxy(lower)-alkanoyl, esterified carboxy(lower)alkanoyl such as lower alkoxycarbonyl(lower)alkanoyl, N- or N,N-di-substituted amino(lower)alkanoyl such as N-or N,N-di(lower)alkylamino(lower)alkanoyl (e.g. N-methyl-(or N,N-diethyl) aminoacetyl, 1(or2)-[N-ethyl(or N,N-diethyl)amino]proprionyl or 1 (or 2)-[N-methyl-N-ethylamino]propionyl) or N-lower alkyl-N-ar(lower)alkylamino(lower)alkanoyl (e.g. 1-(or 2)-[N-methyl-N-benzylamino]propionyl) or aryloxy(lower)alkanoyl such as phenoxyacetyl, tolyloxyacetyl, 2(or 3 or 4)-chlorophenoxyacetyl, 2-[2(or 3 or 4)-chlorophenoxy]propionyl, 2(or 3 or 4)-nitrophenoxyacetyl or 2(or 3 or 4)methoxyphenoxyacetyl); aroyl such as benzoyl, naphthoyl or toluoyl and the like.

Lower alkoxycarbonyl moieties may be methoxycarbonyl, ethoxycarbonyl, propoxycarbonyl, isopropoxycarbonyl, butoxycarbonyl, t-butoxycarbonyl and the like.

Lower alkylsulfamoyl moieties may be methylsulfamoyl, ethylsulfamoyl, propylsulfamoyl, isopropylsulfamoyl, butylsulfamoyl, pentylsulfamoyl and the like.

A heterocyclic group designated $R_1$ may be an aromatic heterocyclic group containing one or more hetero atom(s) selected from a nitrogen atom, a sulfur atom and an oxygen atom, for example, thienyl, furyl, pyrrolyl, thiazolyl, thiadiazolyl, tetrazolyl, pyridyl, pyrimidinyl, quinolyl, isoquinolyl, benzothienyl, indolyl or purinyl.

Esterifed carboxy groups designated $R_2$ and $R_3$ may be lower alkoxycarbonyl such as methoxycarbonyl, ethoxycarbonyl, propoxycarbonyl, isopropoxycarbonyl, butoxycarbonyl, t-butoxycarbonyl; halo(lower)alkoxycarbonyl such as the haloanalogues of the abovementioned lower alkoxycarbonyl (e.g., 2-bromoethoxycarbonyl, 2-chloroethoxycarbonyl, 2(or 3)-chloropropoxycarbonyl, 2 (or 3)-bromopropoxycarbonyl, 2,2-dichloroethoxy-carbonyl or 2,2,2-trichroloethoxycarbonyl); hydroxy(lower)alkoxycarbonyl such as 2-hydroxyethoxycarbonyl or 2(or 3)hydroxypropoxycarbonyl; lower alkoxy(lower)alkoxycarbonyl such as 2-methoxyethoxycarbonyl, 2-ethoxyethoxycarbonyl or 2(or 3)-methoxy(or ethoxy)-propoxycarbonyl; aryloxycarbonyl such as phenoxycarbonyl, tolyloxycarbonyl, xylyloxycarbonyl or p-chlorophenoxycarbonyl; ar(lower)alkoxycarbonyl such as benzyloxycarbonyl, p-bromobenzyloxycarbonyl, O-methoxybenzyl-oxycarbonyl or phenethyloxycarbonyl; ar(lower)alkoxy(lower)alkoxycarbonyl such as 2-(benzyloxyl)ethoxycarbonyl or 2(or 3)-(benzyloxy)propoxycarbonyl; aryloxy(lower)alkoxycarbonyl such as 2-(phenoxy)ethoxycarbonyl or 2(or 3)-(phenoxy)propoxycarbonyl; Nor N,N-(di)-substituted amino(lower)alkoxycarbonyl such as Nor N,N-(di)-(lower)alkylamino(lower) alkoxycarbonyl (e.g., 1(or 2)-[N-methyl(or N,N-dimethyl)-amino]ethoxycarbonyl, 1(or2)-[N-ethyl(or N,N-diethyl)amino]ethoxycarbonyl, or 1(or 2)-N-methyl-N-ethylamino)ethoxycarbonyl or lower alkyl-N-ar(lower)alkylamino(lower)alkoxycarbonyl (e.g. 2-(N-methyl-N-benzylamino)ethoxycarbonyl) and the like, and further $R_2$ and $R_3$ may be same or different.

Lower alkyl substituted with oxo includes lower alkanoyl such as formyl, acetyl, propionyl, butyryl, isobutyryl, valeryl, isovaleryl or pivaloyl and lower alkanoyl(lower)alkyl such as formylmethyl, acetonyl, 2-formylethyl, 3-formylpropyl or butyrylmethyl. The carbonyl group thereof may be protected with suitable protecting group, and thus protected carbonyl group in this invention means a group given by protecting the carbonyl with conventionally employed protecting group for a carbonyl. Suitable examples of such protected carbonyl groups are acetal, cyclic-acetal, thioacetal, cyclic-thioacetal, cyclicmonothioacetal or acylal types of group. Examples of these lower alkyl groups containing such protected carbonyl group are gem-di-(lower)alkoxy(lower)alkyl (e.g., dimethoxymethyl, 1,1-dimethoxyethyl, diethoxymethyl, dipropoxymethyl, 2,2-diethoxyethyl or 2,2-diethoxypropyl; gem-lower alkylenedioxy(lower)alkyl (e.g. 1,3-dioxolan-2-yl, 2-methyl-1,3-dioxolan-2-yl, 4-methyl-1,3-dioxolan-2-yl, 4,5-dimethyl-1,3-dioxolan-2-yl, 1,3-dioxan-2-yl, 2-methyl-1,3-dioxan-2-yl, 1,3-dioxolan-2-yl-methyl, 2-methyl-1,3-dioxolan-2-yl-methyl or 3-(1,3-dioxolan-2-yl)propyl); gem-di-(lower)alkylthio(lower)-alkyl (e.g., dimethylthiomethyl, 1,1-dimethylthioethyl, diethylthiomethyl or 2,2-diethylthioethyl); gem-lower alkylenedithio(lower)alkyl (e.g. 1,3-dithiolan-2-yl, 2-methyl-1,3-dithiolan-2-yl, 4-methyl-1,3-dithiolan-2-yl, 4,5-dimethyl-1,3-dithiolan-2-yl, 1,3-dithian-2-yl, 2-methyl-1,3-dithian-2-yl, 1,3-dithiolan-2-yl-methyl, 2-methyl-1,3- dithiolan-2-ylmethyl or 3-(1,3-dithiolan-2yl)propyl); and gem-di(lower)alkanoyloxy(lower)alkyl (e.g., diacetoxymethyl, 1,1-diacetoxyethyl, dipropionyloxymethyl or 2,2-dipropionyloxyethyl); 5 or 6-membered saturated 1-oxa-3-thioheterocyclic-1-yl-(lower)alkyl (e.g., 1,3-oxathiolan-2-yl, 2-methyl-1,3-oxathiolan-2-yl, 4-methyl-1,3-oxathiolan-2-yl, 4,5-dimethyl-1,3-oxathiolan-2-yl, 1,3-oxothian-2-yl, 2-methyl-1,3-oxothian-2-yl, 1,3-oxathiolan-2-ylmethyl, 2-methyl-1,3-oxathiolan-2-ylmethyl or 3-(1,3-oxathiolan-2-yl)propyl).

A 5 or 6-membered saturated N-containing heterocyclic-1-yl) group may be one which may contain additional one or more hetero atom(s) selected from nitrogen, sulfur and oxygen atoms such as pyrrolidin-1-yl, piperidino, imidazolidin-1-yl, morpholino or thiomorpholino, and it may be optionally substituted with hydroxy, lower alkyl or hydroxy(lower)alkyl such as hydroxymethyl, 2-hydroxyethyl, 2-hydroxypropyl or 3-hydroxypropyl.

The other terms of each lower alkoxyimino, N'- or N',N'-di-(lower)alkylamino(lower)alkylimino, hydroxy(lower)alkylamino, N'- or N',N'-di(lower)alkylamino(lower)alkylamino and hydroxy(lower)alkylamino will be clearly defined by applying optionally the above given exemplifications of the terms to them.

Included in this general formula is 2-cyano-1,4-dihyro-6-methyl-4-(3-nitrophenyl)-3,5-pyridinedicarboxylic acid, 3-methyl-5-(1-methylethyl)ester.

While the above described 1,4-dihydropyridines are preferred, it is to be understood that complexes may be formed with other 1,4-dihydropyridines.

All of the dihydropyridine derivatives which contain an asymmetric carbon atom when totally synthesized comprise racemates consisting of two enantiomers designated (+) and (−) as a consequence of the presence of the asymmetric carbon, for example, at the 4 position. These enantiomers may be resolved and isolated in ways known to those skilled in this art, such as, for example, by chiral chromatography of the racemate or by other means.

The polyoxypropylene-polyoxyethylene block copolymers are known materials which are commercially available or may be prepared by those skilled in the art. These block copolymers are prepared by the sequential addition of propylene oxide and ethylene oxide to propylene glycol and have the general structure:

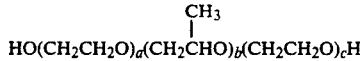

when a, b and c are selected to provide a weight average molecular weight from about 1000 to or over about 16,000. These block copolymers may contain from about 10 to about 80% by weight of oxyethylene units. Preferred block copolymers are commercially available as Pluronic F-127 which has a melting point of 56° C., a weight average molecular weight of 12,000; and a content of 70% oxyethylene units, and Pluronic F-68 which has a melting point of 47° C.; a weight average molecular weight of 6,000 and a content of 80% oxyethylene groups.

The complex may be formed by contacting the 1,4 dihydropyridine with the block copolymer in the presence of a suitable solvent. Suitable solvents include absolute ethanol, methylene chloride, isopropanol, propanol, n-butanol and chloroform. The procedure may be carried at from 25°–90° C. and under atmospheric pressure or superatomospheric pressure. Generally the ratios of 1,4-dihydropyridine: polyoxypropylene-polyoxyethylene block copolymers may be from 1:1 to 1:10 (w/w) preferably from about 1:5 w/w and an amount of the 1,4-dihydropyridine may be employed that will provide a concentration of 1–100 μl/mg and preferably 6–15 μl/mg of solvent to 1,4-dihydropyridine. Any suitable reactor may be utilized although a glass or stainless steel reactor is preferred. The complex may be recovered from the reaction mixture by vacuum evaporation or by other suitable procedures. In the alternative the reaction mixture may be used directly for the preparation of a sustained release dosage formulation.

As shown in FIG. 1, when the complex of nilvadipine and polyoxypropylenepolyoxyethylene comes into contact with water in a physiological environment, it is converted into a solution $N_s$ that is subjected to two competing phenomena: (a) absorption through the biological membrane such as the gastrointestinal mucosa in the $N_m$ state or (b) precipitation in the lowest energy equilibrium solid state ($N_p$). The solid equilibrium state $N_p$ form is not bioabsorbed and the extent of the conversion of $N_s$ to $N_p$ determines the bioavailability of nilvadipine or the particular 1,4-dihydropyridine that is employed.

The sustained release formulation, which is also the subject of this invention, is designed for 1,4-dihydropyridine compounds having the following properties:

(a) poor water solubility which requires conversion to highly water soluble complex forms or polymorphs for sustained release delivery;

(b) water soluble forms or polymorphs which convert to equilibrium states having reduced water solubility and as a result exhibit little or no bioabsorption.

The conversion to different forms is due to water or any constituent in the physiological environment that competes for the ligand in the complex causing displacement of the drug.

The sustained release formulations may comprise: (a) an erodible homogeneous matrix in a tablet, caplet or other geometrical shaped dosage form that when contacted with water will release the active components by causing successive layers of the dosage form to sequentially hydrate or solvate. As the successive layers are hydrated or solvated, the drug is released only from that region of the dosage form. The successive "onion like" dry layers do not have any channels or tortuous paths that could potentially contribute to the formation of microenvironments of a saturated solution of the drug. In sustained release dosage forms of 1,4-dihydropyridine, it is advantageous to avoid the formation of channels in the matrix because if such channels are blocked the drug will precipitate and as a result will not be bioavailable.

Figure 4:
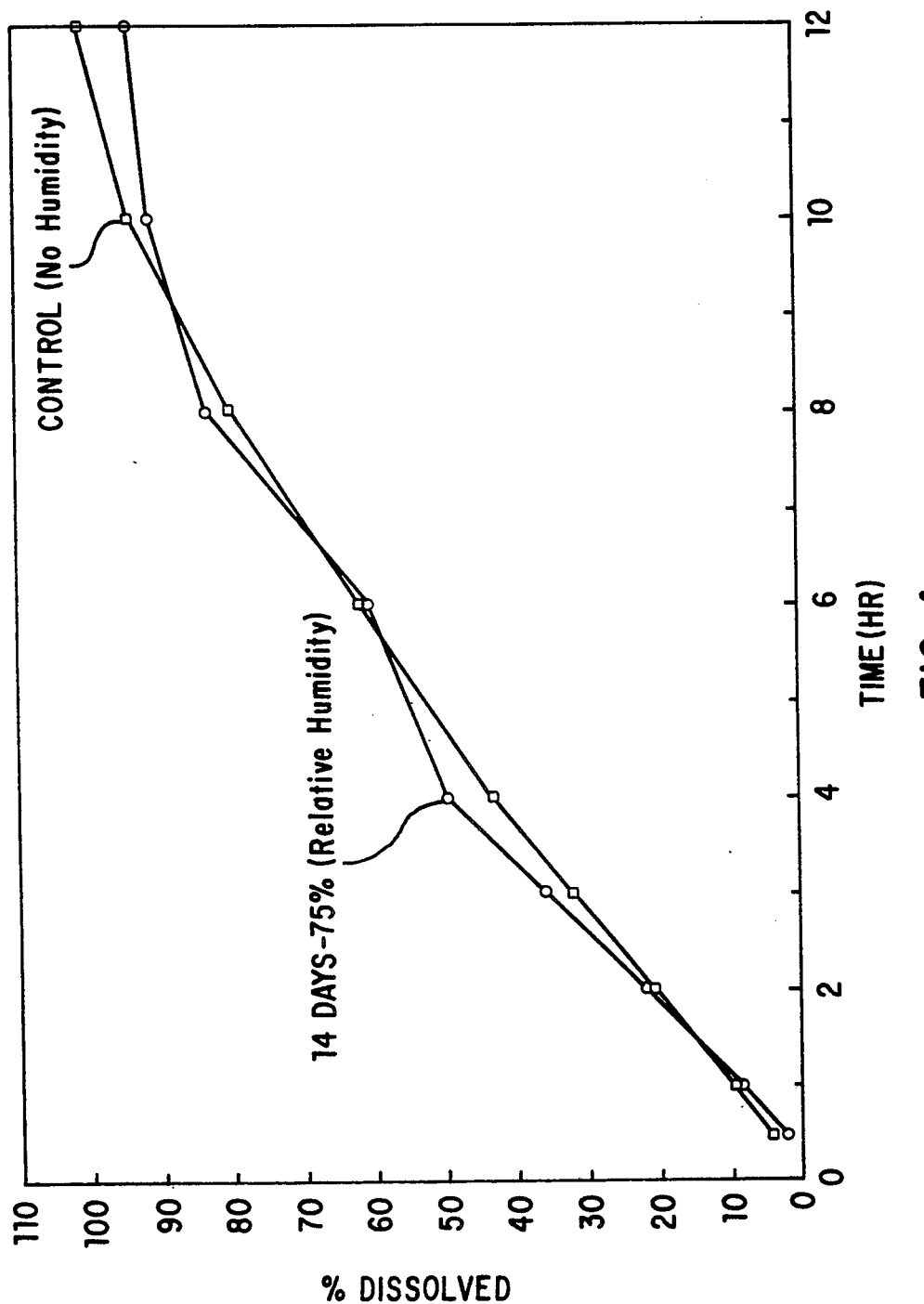
FIG. 4 is a graph which depicts the effect of 14 days of 75% relative humidity on the dissolution profiles of SR tablets containing 10 mg of nifedipine in simulated intestinal fluid.

It is believed that the interaction of polyoxypropylene-polyoxyethylene block copolymers with 1,4-dihydropyridines will prevent immediate hydration of the polymer-drug complex, however, the inventors do not wish to be bound by any theoretical basis on which the invention operates. The selection of a suitable block-copolymer will permit the formation of a relatively stable complex that will exhibit a proper degree of resistance to attack by water. FIG. 4 sets forth the effect of 75% relative humidity on the dissolution in water of a 1:5 complex of nifedipine and Pluronic F-127 As noted hereinabove, generally from 1:1 to 1:10 weight percent of drug to block copolymer may be used. In the case of nilvadipine and Pluronic F-127 the ratio of 1:5 weight percent of drug to Pluronic F-127 was found to be optimum.

It is preferred to react the drug in a non-chlorinated solvent such as a straight or branched chain lower alkanol having 1-7 carbon atoms such as methanol, ethanol, n-propanol, n-butanol and the like although other non-reactive solvents may be employed.

A pharmaceutical excipient which is a water soluble cellulose polymeric derivative that does not cause disintegration may be utilized in the preparation of the sustained release dosage forms. The proportion of excipient to complex will be varied so that the finished dosage form will have the desired pharmacologically effective amount of the drug. These excipients should be selected so that the molecular weight is sufficient that on contact with water they will generate a low viscosity transient gel by swelling which prevents nucleation of the drug in the solution state. Suitable celluose polymeric materials include hydroxypropyl cellulose (L-HPC) and hydroxy propylmethyl cellulose (HPMC).

Sustained release formulations of 1,4-dihydropyridine complex may be prepared with hydroxypropyl methyl cellulose having a molecular weight which provides a viscosity of 9-30 cps at 20° C. as a 2% w/w aqueous solution in water. A quick release formulation may be prepared with 3-8 cps (2% $H_2O$-20° C.) hydroxypropyl methyl cellulose and the 1,4-dihydropyridine complex.

In the preparation of sustained release formulations of complexed 1,4-dihydropyridine, it has been found that the selection and blending of water soluble cellulose derivatives having different molecular weights will provide formulations that deliver complexed 1,4-dihydropyridines for oral absorption at different rates. For example, the use of a hydroxypropylmethyl-cellulose polymer having a molecular weight that exhibits a viscosity of 6 cps at 20° C. as a 2% w/w solution in water with a complex of nilvadipine-polyoxypropylene-polyoxyethylene copolymer will have a quick release rate.

A quick release formulation may be prepared with a ratio of 0.15 to .1 to 0.5 to 1 of 6 cps hydroxypropylmethyl cellulose to nilvadipine-polyoxypropylene-polyoxyethylene block copolymer complex. A 70:30 to 30:70 blend of a 6 cps and 15 cps (2% w/w solution in water at 20° C.) hydroxypropylmethyl cellulose polymer with from 2:1 to 4:1 of nilvadipine-nilvadipine-polyoxypropylene-polyoxyethylene block copolymer complex may be used to prepare a sustained release formulation. Sustained release formulations of other 1,4-dihydropyridine may also be prepared using other water soluble cellulose derivatives which exhibit the desired delivery rates.

The addition of moisture free carbohydrate excipients preferably materials such as lactose, in amounts of from 10-50% by weight of the formulation facilities the slow controlled erosion of the low viscosity transient gel formed by the hydration of the matrix of the complex of the drug block copolymer and the low viscosity excipient which is a water soluble cellulose derivative.

As used herein, the term quick release means a dosage formulation that delivers 100% of the drug in 10 to 30 minutes. The term sustained release is used to include a dosage formulation that delivers approximately a constant fraction of the total dose over 3 to 24 or preferably 12 to 24 hours.

EXAMPLE 1

Complex Formation

In a clean stainless steel beaker is placed 1.56 kg of ethanol U.S.P. (95%) which is warmed to about 45° C. While stirring continuously at that temperature, 1.0 kg of Pluronic F-127 is added to the warm ethanol and the mixture is stirred until the Pluronic F-127 completely dissolves and 0.2 kg of nilvadipine is added in divided amount so that the ratio of nilvadipine to Pluronic F-127 is 1:5 w/w. A clear deep orange colored solution was obtained that contained the nilvadipine-Pluronic F-127 complex.

EXAMPLE 2

Granulation

To 1.5 kg of cps HPMC and 1.5 kg of 15 cps HPMC in a Hobart mixer is added the warm (40°-42° C.) nilvadipine-Pluronic F-127 complex ethanol solution of Example 1. The Hobart mixer is set at medium speed and mixing is carried out for 5 minutes when 0.75 kg of anhydrous lactose is added in small increments. After the lactose is added, mixing is continued at medium speed for 5-10 minutes. A wet granulation is obtained which is vaccum dried in trays under controlled conditions.

The granulate is evenly spread in lined trays and placed in a vacuum oven at 40°-45° C. The contents are vacuum dried over a 16-24 hour period until a moisture level of 1.0% is achieved. Rapid drying and temperatures over 45° C. are to be avoided to prevent the conversion of the drug-polymer complex into an insoluble form of the drug by crystallization.

The dried granules are sieved through a 25 mesh U.S.P. sieve, placed in a V-blender and combined with 0.050 kg of magnesium stearate and mixed for 5-10 minutes until a homogeneous mixture is obtained. At this point the granules are ready for tableting as the sustained release layer of a bilayer sustained release tablet.

The quick release portion is prepared from a nilvadipine complex prepared from 0.15 kg of nilvadipine; 0.75 kg of Pluronic F-127 and 1.17 kg of ethanol U.S.P. (95%).

A Hobart mixer is loaded with 0.25 kg of 6 cps HPMC with the mixing speed set on low speed. A warm (40°-45° C.) alcoholic solution of the complex is added in small increments to assure that the contents are uniformly mixed. The Hobart mixer is set at medium speed for 5 minutes and 3.80 kg of anhydrous lactose is added in small incremental amounts. Mixing is continued for 5-10 minutes at medium speed. The granulation is then vacuum dried and sieved through a 25 mesh U.S.P. screen, placed in a V-blender and mixed with 0.050 kg. of magnesium stearate and mixed for 5-10 minutes until a homogenous mixture is obtained.

Tablet Preparation

A bilayer tablet press that had been separately provided with quick release and sustained release granulation. The tooling size is 13/32" (FFBE) for 12 mg and 16 mg size tablets and 7/16" (FFBE) for 20 mg size tablets.

The following individual layer weights were used:

|        | Nilvadipine |       | Granulate |        |
|--------|-------------|-------|-----------|--------|
|        | Q.R.        | S.R.  | Q.R.      | S.R.   |
| 20 mg  | 8 mg        | 12 mg | 279 mg    | 312 mg |
| 16 mg  | 8 mg        | 8 mg  | 279 mg    | 208 mg |
| 12 mg  | 8 mg        | 4 mg  | 279 mg    | 104 mg |

At different times in the tablet compression process, the weights of the individual layers were checked and adjusted, if necessary, similarly for each dose strength of the tablet measurements for friability, thickness and hardness were taken at different intervals during the entire run.

EXAMPLE 3

Figure 2:
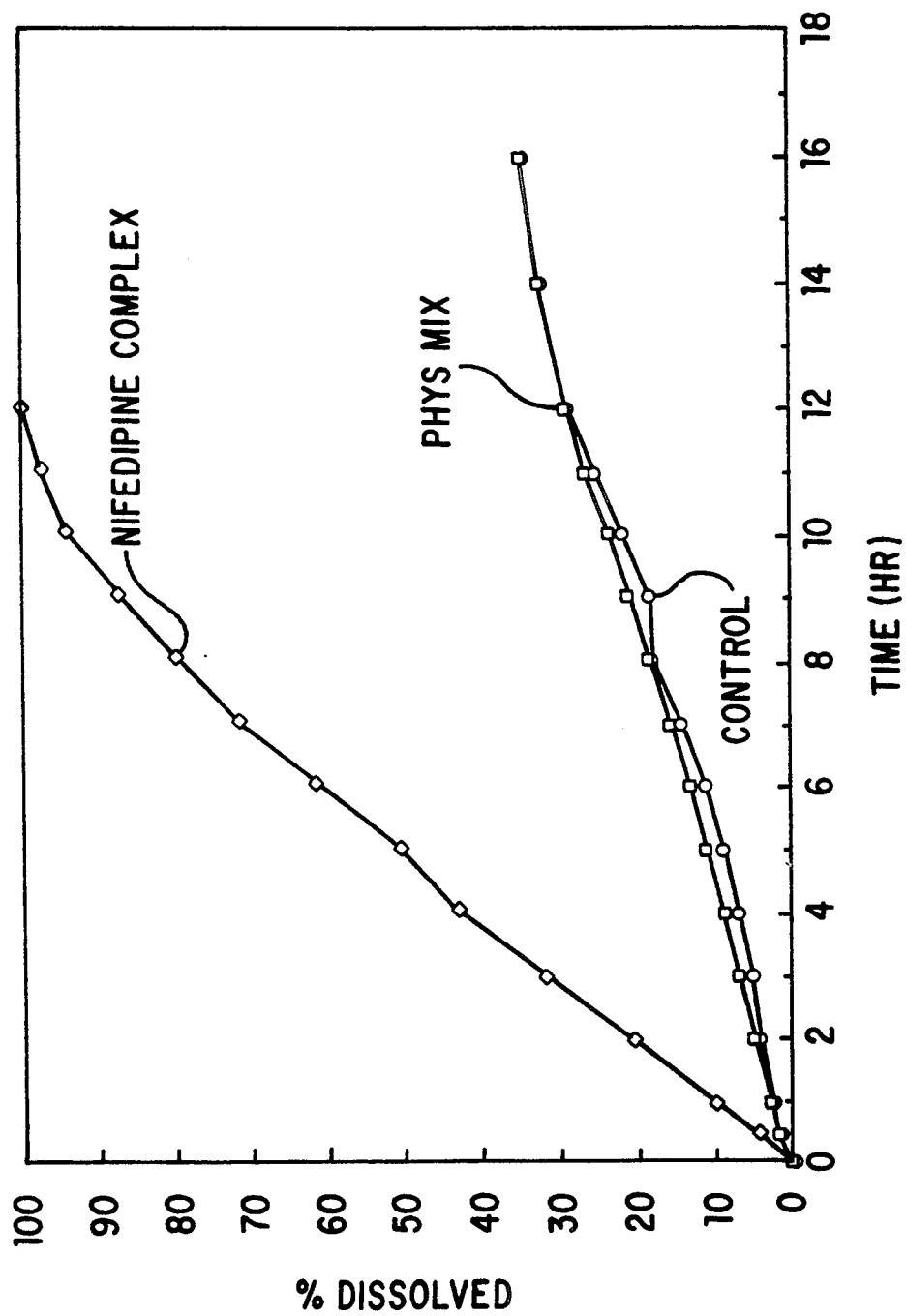
FIG. 2 is a graph which compares the dissolution profiles of nifedipine formulations in simulated intestinal fluid.

By using procedures that are analogous to Example I, a nifedipine-complex is prepared and tableted with each tablet containing 10 mg of nifedipine. Tablets containing 10 mg of nifedipine in a physical mixture with Pluronic F-127 are compared with tablets containing 10 mg of nifedipine without Pluronic F-127 and with tablets containing 10 mg of nifedipine complexed with Pluronic F-127 as shown in FIG. 2. The physical mixture and the complex contained the following:

|                | Physical Mix and Complex % (w) | Control % (w) |
|----------------|-------------------------------|---------------|
| Nifedipine     | 4                             | 4             |
| Pluronic F-127 | 16                            | —             |
| HPMC 15 cps    | 75                            | 75            |
| Lactose        | 4                             | 20            |
| Mg stearate    | 1                             | 1             |

Figure 3:
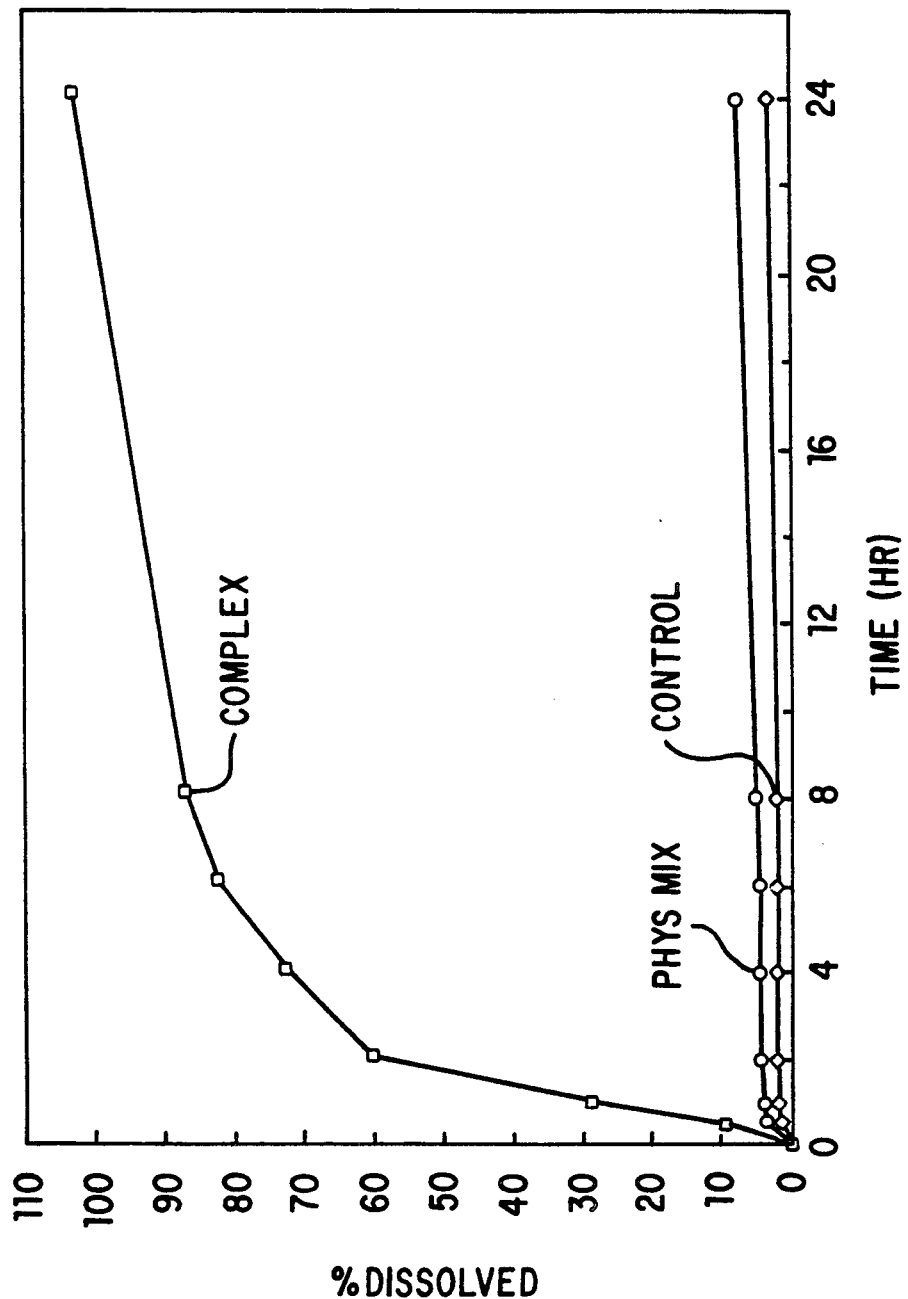
FIG. 3 is a graph which compares the dissolution profiles of bilayer tablets of nilvadipine formulations in simulated intestinal fluid dissolution medium containing 0.4% Tween 20.

The complex was prepared by dissolving the nifedipine and the Pluronic F-127 in ethanol at about 40° C. and thereafter dispersing the ethanol solution on the lactose according to the general procedure of Example 2. The physical mixture is made by admixing all excipients in the absence of ethanol. The dissolution profile for 16 mg bilayer nilvadipine tablets is shown in FIG. 3 wherein the nilvadipine complex with HPMC and the physical mixture of nilvadipine had the following formulation:

|                | Physical Mix and Sustained Release Layer (8 mg) | Control (SR) |
|----------------|--------------------------------------------------|--------------|
| Nilvadipine    | 4%                                               | 4%           |
| Pluronic F-127 | 20%                                              | —            |
| HPMC 6 cps     | 30%                                              | 30%          |
| HPMC 15 cps    | 30%                                              | 30%          |
| Mg stearate    | 1%                                               | 1%           |
| Lactose        | 15%                                              | 35%          |
|                | Quick Release (8 mg)                             | Control (QR) |
| Nilvadipine    | 3%                                               | 3%           |
| Pluronic F-127 | 15%                                              | —            |
| HPMC 6 cps     | 5%                                               | 5%           |
| Lactose        | 76%                                              | 91%          |
| Mg Stearate    | 1%                                               | 1%           |

The tablets were prepared according to the general procedures set forth hereinabove. The data set forth in FIG. 2 and FIG. 3 establish the effectiveness of the complexed 1,4-dihydropyridines as a dosage formulation.

EXAMPLE 4

Figure 5:
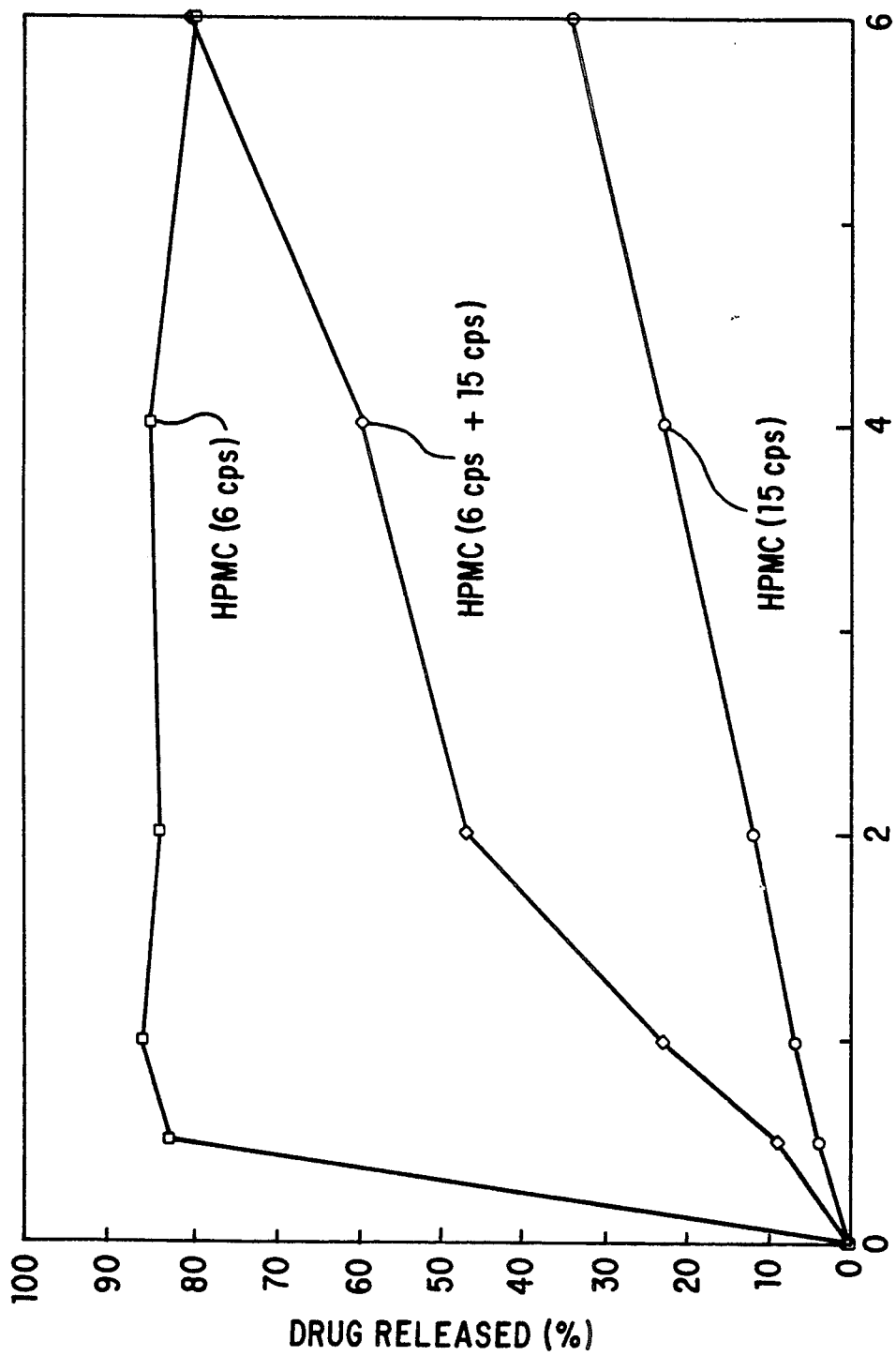
FIG. 5 is a graph which composes the dissolution profiles of 10 mg QR and SR formulation of nifedipine simulated intestinal fluid at 37° C.

FIG. 5 is sets forth the release rate for one quick release formulation of nifedipine-Pluronic F-127 complex and two sustained release formulations of the same complex. It can be seen that by varying the type or by blending different types of hydroxypropylmethyl cellulose (HPMC), different release rates may be obtained.

The 6 cps, 6 cps and 15 cps and 15 cps formulation have the following components:

|                | 6 cps | 6/15 cps | 15 cps |
|----------------|-------|----------|--------|
| Nifedipine     | 3     | 3        | 3      |
| Pluronic F-127 | 12    | 12       | 12     |
| HPMC           | 5     | 30/30    | 60     |
| Lactose        | 79    | 24       | 24     |
| Mg Stearate    | 1     | 1        | 1      |

EXAMPLE 5

Figure 6:
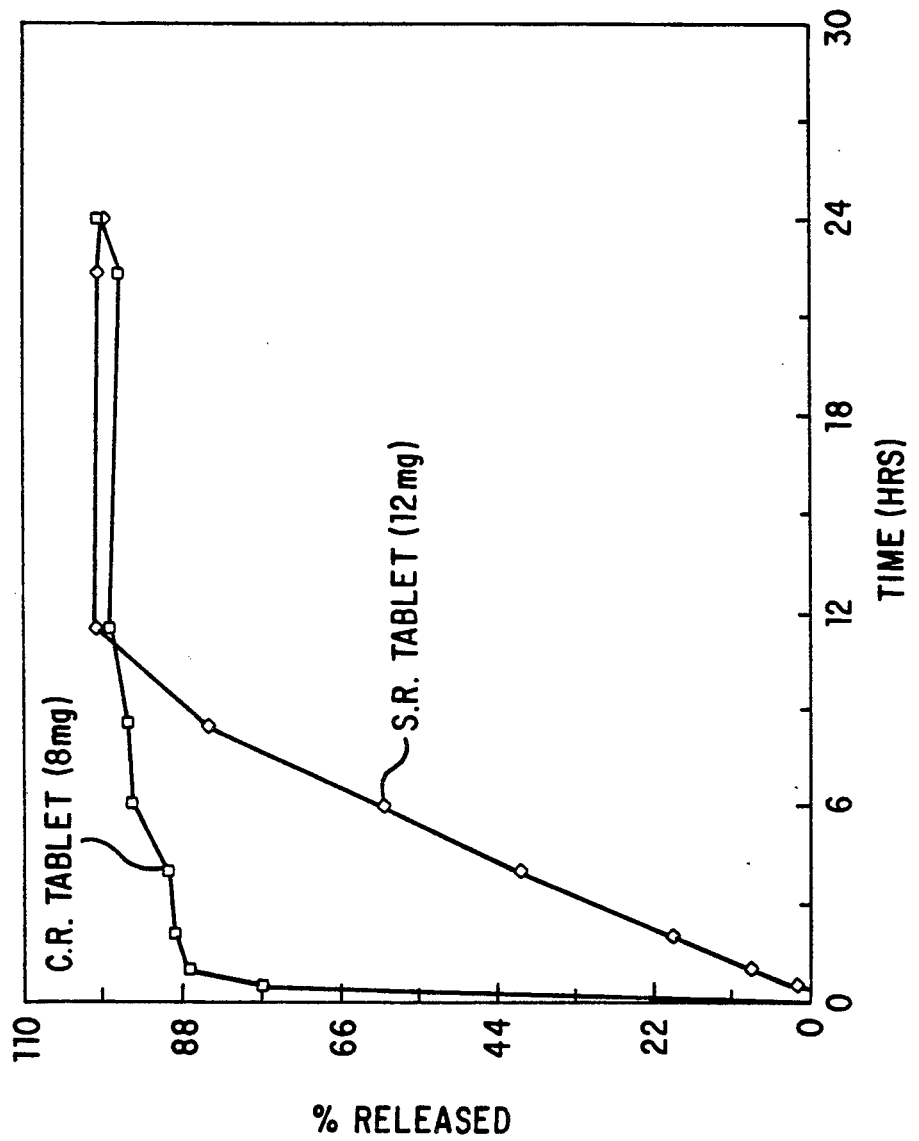
FIG. 6 is a graph that gives the shows the release rates of quick release and sustained release tablets of nilvadipine-polyoxyethylene-polyoxypropylene complex.

FIG. 6 is a graph that sets forth the release rates of tablets of a quick release and a sustained release formulation of nilvadipine-Pluronic F-127 complex with different types of HPMC. These data may be utilized to select formulations to give desired release rates. The quick release and sustained release formulations are from Example 2.

Figure 7:
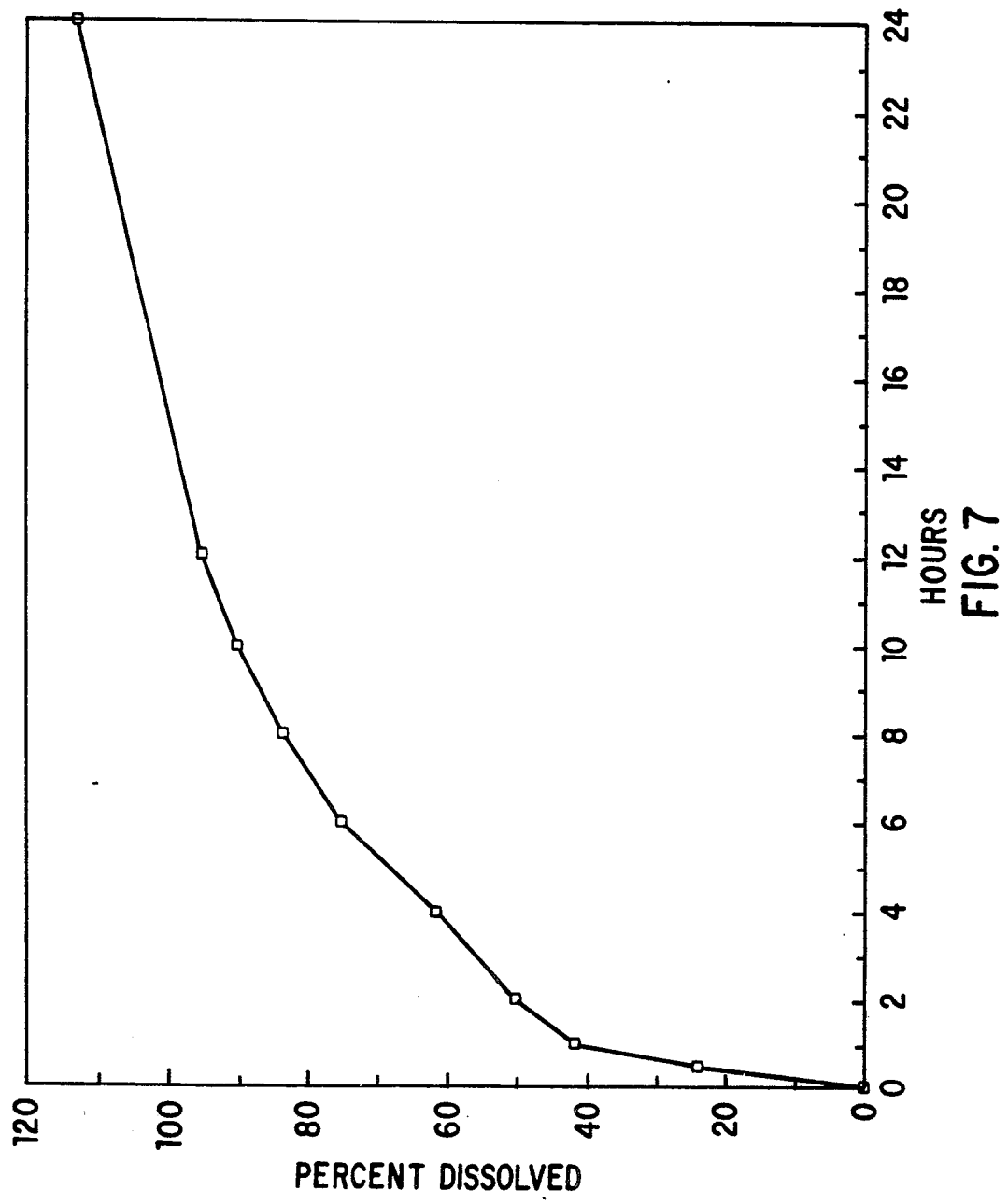
FIG. 7 is a graph that illustrates the release rate of a 20 mg bilayer tablet of QR and SR nilvadipine complex.

FIG. 7 is a graph that illustrates the release rate of a 20 mg bilayer tablet that is made of 8 mg of the quick release and 12 mg of the sustained release formulations shown on FIG. 6. These data show the result of the simultaneous administration of selected amounts of a quick release and a sustained release formulation in a bilayer tablet.

We claim:

1. A complex which comprises a 1,4-dihydropyridine complexed with a block copolymer having the general structure:

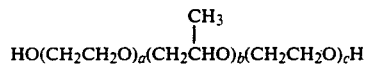

wherein a, b and c are selected to provide a molecular weight of from about 1,000 to about 16,000 and from about 10% to about 80% by weight of oxyethylene units said complex being obtained by reacting a 1:1 to 1:10 ratio of 1,4-dihydropyridine and said block copolymer in solution at a temperature of 25°-90° C. and thereafter recovering said complex.

2. A complex as defined in claim 1 wherein the 1,4-dihydropyridine is selected from the group consisting of nilvadipine, nitrendipine, nisoldipine, niludipine, nicardipine, nifedipine, felodipine and nimodipine.

3. A complex as defined in claim 1 wherein the 1,4-dihydropyridine is the general formula:

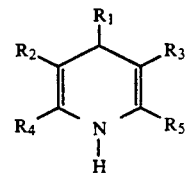

wherein $R_1$ is aryl;

R₂ and R₃ are the same or different and are ester groups or carboxy groups; and

R₄ and R₅ are selected from hydrogen, cyano, lower alkyl, or substituted lower alkyl in which the substituent is cyano, hydroxy, acyloxy, hydroxyimino, hydrazono lower alkoxyimino, hydroxy(lower)alkylimino, hydrazino, hydroxy(lower alkylamino, N'or N', N'-di(lower)alkylamino(lower)alkylamino, a 5 or 6 membered saturated N-containing heterocyclic-1-yl which may have hydroxy, lower alkyl or hydroxy(lower)alkyl, or oxo wherein the thus formed carbonyl may be protected with a suitable protecting group, provided that when one of R₄ and R₅ is hydrogen or lower alkyl, both of them are a group selected from cyano and said substituted lower alkyl, or R₄ is hydrogen or lower alkyl and R₃ and R₅ are combined to form a group of the formula:

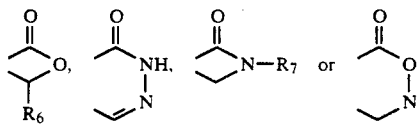

wherein R₆ is hydrogen or methyl and R₇ is 2-(N,N-diethylamino)ethyl or 2-hydroxyethyl.

4. A complex as defined in claim 1 wherein the 1,4-dihydropyridine is nilvadipine.

5. A complex as defined in claim 4 wherein the block copolymer has 70% by weight of oxyethylene units and a weight average molecular weight of about 12,000.

6. A complex as defined in claim 5 wherein the ratio of nilvadipine to block copolymer is from 1:1 to 1:10 by weight.

7. A complex as defined in claim 6 wherein the ratio is about 1:5.

8. A complex as defined in claim 1 wherein the 1,4-dihydropyridine is nifedipine.

9. A complex as defined in claim 1 wherein the block copolymer has 70% by weight of oxyethylene units and a weight average molecular weight of about 12,000.

10. A complex as defined in claim 9 wherein the ratio of nifedipine to block copolymer is from 1:1 to 1:10 by weight.

11. A complex as defined in claim 10 wherein the ratio is about 1:5.

12. A pharmaceutical composition which comprises the complex of claim 1 and a pharmaceutical excipient.

13. A pharmaceutical composition which comprises the complex of claim 4 and a pharmaceutical excipient.

14. A pharmaceutical unit dosage form which comprises the complex of claim 8 and a pharmaceutical excipient.

15. A pharmaceutical unit dosage form as defined in claim 14 wherein said pharmaceutical dosage form is a tablet.

16. A pharmaceutical unit dosage form as defined in claim 14 wherein said pharmaceutical dosage form is a capsule.

17. A pharmaceutical unit dosage form as defined in claim 15 wherein said tablet is a bilayer tablet which contains a quick release layer and a sustained release layer.

18. A sustained release dosage formulation which comprises one or more water soluble cellulose derivatives having a molecular weight which provides a viscosity in water of 9 to 30 cps at 20° C. as a 2% w/w aqueous solution and a 1,4-dihydropyridine complex with a polyoxypropylene-polyoxyethylene copolymer complex according to claim 1.

19. A sustained release dosage formulation as defined in claim 18 wherein the water soluble cellulose derivative is a blend of 6 cps and 15 cps hydroxypropyl methyl cellulose and the complex is a nilvadipine-polyoxypropylene polyoxyethylene copolymer complex.

20. A sustained release dosage formulation as defined in claim 18 wherein the water soluble celluose derivative is a blend of 6 cps and 15 cps hydroxypropyl methyl cellulose and the complex is a nifedipine-polyoxypropylene-polyoxyethylene copolymer complex.

21. A quick release dosage formulation which comprises one or more water soluble cellulose derivatives having a molecular weight which provides a viscosity in water of 3 to 8 cps at 20° C. as a 2% solution in water and a 1,4-dihydropyridine complex with a polyoxypropylene-polyoxyethylene copolymer complex according to claim 1.

22. A quick release dosage formulation as defined in claim 21 wherein the water soluble cellulose derivative is 6 cps hydroxypropyl methyl cellulose and the complex is a nilvadipine-polyoxypropylene-polyoxyethylene copolymer complex.

23. A quick release dosage formulation as defined in claim 21 wherein the water soluble cellulose derivative is 6 cps hydroxypropyl methyl cellulose and the complex is a nifedipine-polyoxypropylene-polyoxyethylene copolymer complex.

24. A complex of nilvadipine and a block copolymer of polyoxypropylene/polyoxyethylene having a content of about 70% oxyethylene units and a weight average molecular weight of about 12,000 which is prepared by reacting said nilvadipine and said block copolymer in a solvent at a temperature of 25°-90° C. to form said complex and thereafter recovering said complex from said solvent.

* * * * *